United States Patent [19]

Spitzer

[11] Patent Number: 4,492,708

[45] Date of Patent: Jan. 8, 1985

[54] ANTIVIRAL BENZIMIDAZOLES

[75] Inventor: Wayne A. Spitzer, Indianapolis, Ind.

[73] Assignee: Eli Lilly and Company, Indianapolis, Ind.

[21] Appl. No.: 424,784

[22] Filed: Sep. 27, 1982

[51] Int. Cl.³ .............. A61K 31/415; C07D 235/30; C07D 235/06

[52] U.S. Cl. .................. 424/273 B; 424/248.4; 424/248.52; 424/248.54; 424/248.55; 424/248.56; 424/248.57; 424/248.58; 424/263; 424/267; 424/270; 544/139; 546/199; 546/271; 548/181; 548/305; 548/306; 548/325; 548/327; 548/329; 548/330; 548/333

[58] Field of Search .......... 548/325, 305, 306, 329, 548/330, 333; 424/273 B

[56] References Cited

U.S. PATENT DOCUMENTS

| | | | |
|---|---|---|---|
| 3,265,691 | 8/1966 | Richter et al. | 544/139 |
| 3,336,191 | 8/1967 | Craig et al. | 424/273 B |
| 3,813,409 | 5/1974 | Haugwitz | 548/181 |
| 3,825,537 | 7/1974 | Haugwitz et al. | 544/55 |
| 4,008,243 | 2/1977 | Wikel et al. | 548/181 |
| 4,026,936 | 5/1977 | Lauer et al. | 546/271 |
| 4,174,454 | 11/1979 | Paget et al. | 548/306 |
| 4,191,832 | 3/1980 | Su et al. | 548/306 |
| 4,230,868 | 10/1980 | Paget et al. | 548/306 |
| 4,316,021 | 2/1982 | Paget et al. | 544/139 |
| 4,338,315 | 7/1982 | Paget et al. | 424/246 |
| 4,338,329 | 7/1982 | Paget et al. | 424/270 |
| 4,344,957 | 8/1982 | Habicht et al. | 424/273 B |

FOREIGN PATENT DOCUMENTS 93791  6/1970  Belgium ............ 548/305

OTHER PUBLICATIONS

*Chemical Abstracts*, 74:124471 b(1971), Shiokawa, Y., et al.
Shiokawa, Y., et al., *Chem. Pharm. Bull.* 1971, 19 (2), 401–8.
Tamm, I., *J. Exp. Med.*, 138, 858 (1973).
CA 80:66925p (1974) [Tamm, I., *J. Exp. Med.*, 138 (4), 858 (1973)].
Ellis, G., et al., *J. Chem. Soc., Perkin Trans. I*, 1974 (8), 903.
Cole, E., et al., *Tetrahedron Letters*, 34, 2925 (1974).
CA 90:137728w (1979) [Tsizin, Y., et al., *Khim. Geterotsikl. Soedin.* 1978, (12), 1680–3].

*Primary Examiner*—Richard A. Schwartz
*Attorney, Agent, or Firm*—Charles W. Ashbrook; Arthur R. Whale

[57] ABSTRACT

Certain N-substituted benzimidazoles are disclosed. The compounds are potent antiviral agents. Pharmaceutical formulations containing such compounds and a method of treating viral infections are provided.

53 Claims, No Drawings

ANTIVIRAL BENZIMIDAZOLES

BACKGROUND OF THE INVENTION

The incidence of viral upper respiratory disease is immense. It has been estimated that nearly a billion cases annually appear in the United States alone. Studies performed in England (Tyrell and Bynoe, 1966) indicated that 74 percent of persons having colds were infected with rhinoviruses. Because more than 80 strains of rhinoviruses are already identified, the development of a practical rhinovirus vaccine is not feasible, and chemotherapy appears to be the more desirable approach.

The ability of chemical compounds to suppress the growth of viruses in vitro is readily demonstrated by using a virus plaque suppression test similar to that described by Siminoff, *Applied Microbiology*, 9(1), 66 (1961).

Certain benzimidazole compounds have been found to possess anti-viral activity, including those compounds found in the following U.S. Pat. Nos. 4,150,028, 4,216,313, 4,293,558, and 4,338,315 (1-thiazolinyl and -thiazinyl keto benzimidazoles); 4,174,454 (alkylidenylmethyl-substituted-1-sulfonylbenzimidazoles); 4,018,790, 4,118,573, 4,196,125, 4,243,813 and 4,316,021 (1-sulfonyl-2,5(6)-substituted benzimidazoles); 4,008,243 (1-thiazolinyl and -thiazinyl benzimidazole esters); 4,230,868 (α-alkyl-α-hydroxybenzyl-substituted-1-sulfonylbenzimidazoles); and 4,118,742, 4,289,782, and 4,338,329 (carbonyl substituted-1-sulfonylbenzimidazoles).

It is the purpose of this invention to provide novel benzimidazole compounds which inhibit the growth of viruses, particularly rhinoviruses, polio viruses, Coxsackie viruses, echo virus, and Mengo virus.

SUMMARY OF THE INVENTION

This invention concerns pharmacologically useful benzimidazole compounds having the formula

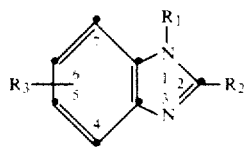

and pharmaceutically acceptable salts thereof, wherein $R_1$ is $C_1-C_8$ alkyl, $C_2-C_8$ alkenyl, $C_3-C_7$ cycloalkyl, $C_5-C_7$ 1-cycloalkenyl, 2-pyridyl, 2-thiazolyl, adamantyl, hydroxy-substituted $C_1-C_8$ alkyl, unsubstituted or substituted phenyl, unsubstituted or substituted benzyl, or $R_4R_5NCH_2-$, where $R_4$ and $R_5$ are independently $C_1-C_3$ alkyl or $R_4$ and $R_5$, when taken together with the nitrogen atom to which they are attached, are pyrrolidino, piperidino, or morpholino;

$R_2$ is hydrogen, amino, $C_1-C_4$ alkylamino, methylmercapto, hydroxy, $C_1-C_4$ acylamino, or 1-hydroxyethyl;

$R_3$ is $C_2-C_8$ alkanoyloxy, unsubstituted or substituted phenylacetoxy, unsubstituted or substituted benzoyloxy, or

Z is oxygen, hydroxyimino, $C_1-C_4$ alkoxyimino, $C_1-C_4$ acyloxyimino, hydrazono, $C_1-C_7$ alkylidene, CHBr, CHCl, CHCN, CHCONH$_2$, or CHCO$_2$(C$_1-$C$_4$ alkyl);

$R_6$ is $C_1-C_7$ alkyl, $C_3-C_7$ cycloalkyl, (C$_3-$C$_7$ cycloalkyl)methyl, 2-(C$_3-$C$_7$ cycloalkyl)ethyl, unsubstituted or substituted benzyl, unsubstituted or substituted phenyl; and $R_3$ is at the 5 or 6 position, subject to the limitation that when $R_2$ is hydroxy, $R_1$ may only be $C_5-C_7$ 1-cycloalkenyl.

This invention additionally provides a method of treatment which comprises administering to a mammal suffering from a viral infection or suspected of developing a viral infection an effective antiviral amount of a benzimidazole defined by the above formula.

A further embodiment of the present invention includes a pharmaceutical formulation useful in the treatment and prophylactic control of viral infections in mammals comprising a benzimidazole defined by the above general formula in combination with a pharmaceutically acceptable carrier or diluent therefor.

DETAILED DESCRIPTION AND PREFERRED EMBODIMENT

The present invention relates to new benzimidazole compounds that are useful as antiviral agents. The benzimidazoles are potent antiviral agents and are accordingly useful in the treatment and control of viral growth, including growth attributable to rhinovirus, polio, coxsackie, echo virus, mengo virus, influenza, and related viral growths.

A preferred group of compounds are the compounds of formula (I) wherein
 (a) $R_1$ is $C_1-C_8$ alkyl,
 (b) $R_1$ is $C_2-C_8$ alkenyl,
 (c) $R_1$ is phenyl,
 (d) $R_1$ is substituted phenyl,
 (e) $R_2$ is hydrogen,
 (f) $R_2$ is amino,
 (g) $R_1$ is $C_3-C_7$ cycloalkyl, and
 (h) $R_3$ is

wherein $R_6$ is phenyl or substituted phenyl.

Especially preferred compounds of formula (I) are those wherein
 (a) $R_1$ is isopropyl,
 (b) $R_1$ is cyclohexyl,
 (c) $R_1$ is phenyl,
 (d) $R_2$ is hydrogen,
 (e) $R_2$ is amino, and
 (f) $R_3$ is

wherein $R_6$ is phenyl and
 (1) Z is oxygen, (2) Z is hydroxyimino,
(3) Z is =CHBr,
(4) Z is =CHCN,
(5) Z is =CHCH$_3$, and
(6) Z is =CHCONH$_2$.

Especially preferred compounds are those wherein R$_3$ is at the 6 position.

The compounds of the invention are prepared by reacting a tautomeric benzimidazole compound of the formula

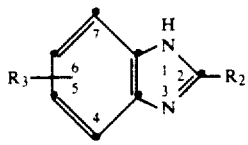
(II)

with a halo compound having the formula R$_1$X wherein R$_1$, R$_2$ and R$_3$ are as defined hereinabove, and X is fluoro, chloro, bromo, or iodo.

Alternatively, the compounds may be prepared according to the following scheme:

SCHEME 1

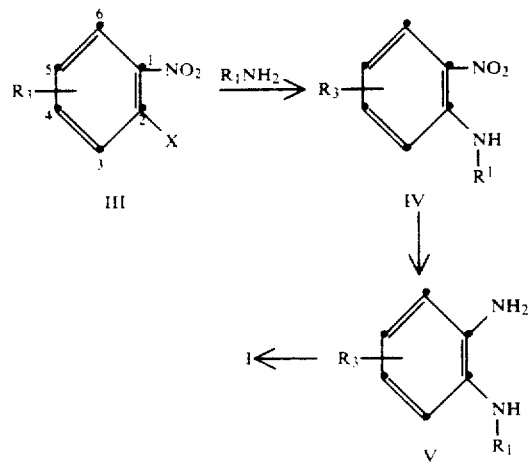

wherein R$_1$, R$_3$, and X are the same as described hereinabove and R$_3$ is at the 4 or 5 position of III, IV, and V.

The term "tautomeric benzimidazole" refers to a benzimidazole reagent which can be substituted at either nitrogen atom with a hydrogen atom. The benzimidazole reactant, unsubstituted on nitrogen and bearing a substituent group at the 5 position of the benzene moiety, has a corresponding tautomeric form wherein the substituent resides alternatively at the 6 position. The isomer mixture can be indicated by numbering the alternate positions as 5(6). As a consequence of such tautomerism, the reaction of a 5(6)-substituted N-unsubstituted benzimidazole with R$_1$X produces isomeric mixtures of 5(6)-substituted N-substituted benzimidazoles.

The term "C$_1$-C$_8$ alkyl" refers to the straight and branched aliphatic radicals of one to eight carbon atoms including methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl, (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methyl-hexyl), 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl), tert-octyl (1,1,3,3-tetramethylbutyl), and the like. The term C$_1$-C$_8$ alkyl includes within its definition the terms "C$_1$-C$_3$ alkyl," "C$_1$-C$_4$ alkyl," "C$_1$-C$_5$ alkyl," "C$_1$-C$_6$ alkyl", and "C$_1$-C$_7$ alkyl."

The term "C$_3$-C$_7$ cycloalkyl" refers to the saturated alicyclic rings of three to seven carbon atoms such as cyclopropyl, methylcyclopropyl, cyclobutyl, cyclopentyl, cyclohexyl, 1-, 2-, 3- or 4-methylcyclohexyl, cycloheptyl, and the like. The term "(C$_3$-C$_7$ cycloalkyl)methyl" refers to a methyl radical substituted with saturated alicyclic rings of three to seven carbon atoms as exemplified in the term "C$_3$-C$_7$ cycloalkyl," such as cyclopropylmethyl, cyclobutylmethyl, cyclopentylmethyl, cyclohexylmethyl, cycloheptylmethyl and the like. The term "2-(C$_3$-C$_7$ cycloalkyl)ethyl" refers to ethyl radicals substituted on the carbon atom in the 2 position with saturated alicyclic rings of three to seven carbon atoms.

The term "C$_5$-C$_7$ 1-cycloalkenyl" refers to alicyclic rings of five to seven carbon atoms which have a double bond in the 1-position, such as 1-cyclopentenyl, 1-cyclohexenyl, 2-, 3-, or 4-methyl-1-cyclohexenyl, 1-cycloheptenyl, and the like.

The term "C$_2$-C$_8$ alkanoyl" refers to the straight and branched aliphatic acyl radicals of two to eight carbon atoms such as acetyl, propionyl, butyryl, 2-methylpropionyl, pentanoyl, hexanoyl, heptanoyl, octanoyl, and the like.

The term "C$_1$-C$_7$ alkylidene" refers to straight and branched alkylidene radicals of one to seven carbon atoms such as methylene, ethylidene, propylidene, isopropylidene, butylidene, isobutylidene, 3-methylbutylidene, n-hexylidene and the like.

The term "C$_1$-C$_4$ alkoxy" includes the straight and branched aliphatic ether radicals of one to four carbon atoms such as methoxy, ethoxy, propoxy, isopropoxy, butoxy, isobutoxy, sec-butoxy, and the like. The term "C$_1$-C$_4$ alkoxyimino" refers to the 0-aliphatic hydroxyimine radical of one to four carbon atoms derived from hydroxylamine. Methoxyamine hydrochloride is available from commercial sources. Other hydroxylamine derivatives are available by alkylation of acetone oxime by C$_1$-C$_4$ alkyl halides followed by acid hydrolysis.

The term "substituted" -phenyl, -benzyl, -phenzoyloxy, and -benzoyloxy refers to those groups substituted on the aromatic ring with one to three of C$_1$-C$_4$ alkyl, C$_1$-C$_4$ alkoxy, fluoro, chloro, bromo, iodo, nitro, amino, or trifluoromethyl. The preferred substituent is that in the 4' or para position of the aromatic ring, especially 4'-methoxy.

In the reaction of a tautomeric benzimidazole II with R$_1$X, the preferred reactants are benzimidazoles bearing 5(6)-substituents which will not react with R$_1$X under the reaction conditions. The benzimidazole II and R$_1$X are normally employed in approximately equimolar quantities, although an excess of either can be used if desired. The reaction can be carried out in any number of unreactive solvents, including acetone, tetrahydrofuran (THF), tertiary amides such as N,N-dimethylformamide (DMF), and chlorinated hydrocarbons such as dichloromethane, dichloroethane and chloroform. The reaction medium may also contain added base to serve as an acid-binding agent. Some examples of suitable bases for this purpose are pyridine, triethylamine, N-methylmorpholine, sodium bicarbonate, and sodium hydride. A preferred solvent medium for the reaction is DMF containing sodium hydride as a base.

The reaction is best carried out at a temperature between 0° C. and the reflux temperature of the solvent system employed. Preferably, the reaction is carried out at 0° C. to room temperature. In this temperature range, the reaction is substantially complete within 1 to 48 hours.

The product of the reaction is a 1-substituted benzimidazole compound, hereinafter called the benzimidazole compound. The product may be isolated by filtering the reaction mixture and concentrating the filtrate to induce crystallization. Alternatively, the reaction mixture can be evaporated to dryness and the residue treated with a suitable solvent such as acetone or methanol to separate and remove any insoluble material. The solution containing the benzimidazole compound is concentrated to crystallize the product or it is evaporated to give a second residue, which is dissolved in methanol, for example. The benzimidazole compound is recovered from the methanol by crystallization. Chromatography over silica gel may also be employed in the purification scheme, either alone or in combination with the above purification steps.

The reaction of the tautomeric benzimidazole II and $R_1X$ generally provides an approximate 1:1 mixture of 5- and 6-substituted benzimidazole compounds. The isomers are separable by fractional crystallization or by chromatography.

The 5(6)-ketobenzimidazole compounds I wherein $R_3$ is $R_6CO$ can be prepared from the corresponding 5(6)-ketobenzimidazoles II by reaction with $R_1X$. The ketobenzimidazole reactant II can be prepared from the appropriate keto o-phenylenediamine by methods known to the benzimidazole art. Belgian published application No. BE No. 752089, Derwent accession No. R/50 93791 discloses the preparation of keto o-phenylenediamines of the formula

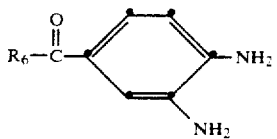

wherein $R_6$ is lower alkyl, cycloalkyl, phenyl or phenyl substituted by halogen, lower alkyl or lower alkoxy. The method of preparation involves the ammonolysis and reduction of a 4-halo-3-nitrophenyl ketone which is prepared by the Friedel-Crafts reaction of either (1) a 4-halo-3-nitrobenzoyl chloride with an appropriate hydrocarbon or (2) a halobenzene with an appropriate acid chloride followed by aromatic nitration. Such methods make available the required keto o-phenylenediamines wherein $R_6$ in the formula above is additionally $C_3$-$C_7$ cycloalkyl, ($C_3$-$C_7$ cycloalkyl)methyl, 2-($C_3$-$C_7$ cycloalkyl)ethyl or benzyl. Alternatively, the keto benzimidazole reactants can be prepared from acetanilide by a Friedel-Crafts acylation with the appropriate derivative of a $C_2$-$C_8$ alkanoic acid, $C_3$-$C_7$ cycloalkyl carboxylic acid, $C_3$-$C_7$ cycloalkylacetic acid, 3-($C_3$-$C_7$ cycloalkyl)propionic acid, phenylacetic acid, benzoic acid or substituted benzoic acid. The resulting 4-ketoacetanilide is nitrated to give a 2-nitro-4-ketoacetanilide. The acetanilide is hydrolyzed to give a 2-nitro-4-ketoaniline. The nitroaniline is catalytically hydrogenated to yield a 4-keto-o-phenylenediamine which is ring closed to provide the appropriate 5(6)-ketobenzimidazole. The following embodiment illustrates in principle the preparation of a 5(6)-ketobenzimidazole compound. 4-Propionylacetanilide is nitrated at 0° C. to yield 2-nitro-4-propionylacetanilide. The acetanilide is hydrolyzed and catalytically hydrogenated to give 4-propionyl-o-phenylenediamine. The phenylenediamine is reacted with cyanogen bromide to give 2-amino-5(6)-propionylbenzimidazole. The propionylbenzimidazole is reacted with isopropyl bromide to provide 1-isopropyl-2-amino-5(6)-propionylbenzimidazole. These methods make available the 5(6)-($C_2$-$C_8$)alkanoyl, 5(6)-($C_3$-$C_7$)cycloalkylcarbonyl, 5(6)-($C_3$-$C_7$)cycloalkylacetyl, 5(6)-[3-($C_3$-$C_7$ cycloalkyl)propionyl], 5(6)-phenylacetyl, 5(6)-benzoyl or the 5(6)-substituted-benzoylbenzimidazole compounds. The 5(6)-ketobenzimidazole compounds are represented by the formula

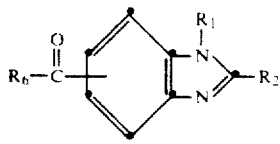

wherein $R_6$ is $C_1$-$C_7$ alkyl, $C_3$-$C_7$ cycloalkyl, ($C_3$-$C_7$ cycloalkyl)methyl, 2-($C_3$-$C_7$ cycloalkyl)ethyl, benzyl, substituted benzyl, phenyl or substituted phenyl, and $R_1$ and $R_2$ are as defined previously.

The intermediate benzimidazole compounds wherein $R_3$ is hydroxy can be prepared from the corresponding 5(6)-hydroxybenzimidazole reactants. The preparation of the required hydroxybenzimidazole compounds begins with the reduction of 4-methoxy-2-nitroaniline to the corresponding 4-methoxy-o-phenylenediamine. The phenylenediamine is ring closed to provide a 5(6)-methoxybenzimidazole by methods known to the benzimidazole art. The methyl ether is cleaved with hydrobromic acid to give a 5(6)-hydroxybenzimidazole. The hydroxybenzimidazole is reacted with the appropriate $R_1X$ to provide the required 1-substituted5(6)-hydroxybenzimidazole compounds.

The phenolic hydroxyl functionality of the 5(6)-hydroxybenzimidazole compounds can be reacted with the anhydrides or chlorides of $C_2$-$C_8$ alkanoic acids, phenylacetic acids or benzoic acids in an aprotic solvent to provide the corresponding esters. The ester products derived from the 5(6)-hydroxybenzimidazole reactants are respectively the 5(6)-($C_2$-$C_8$)alkanoyloxy-, 5(6)-phenylacetoxy-, or 5(6)-benzoyloxy-benzimidazole compounds. Alternatively the hydroxybenzimidazole compounds can be esterified with the appropriate acid reactant in the presence of 1,1'-carbonyldiimidazole in dimethylformamide.

The benzimidazole compounds which are required as starting materials in the foregoing process can be prepared according to a variety of methods known to the benzimidazole art. The preparation of a variety of benzimidazoles is well documented in Weissberger's *The Chemistry of Heterocyclic Compounds. Imidazole and Its Derivatives*, Interscience Publishers Co., New York, 1953. The 2-aminobenzimidazole reactants can be prepared by cyclizing the appropriate o-phenylenediamines with cyanogen bromide as described by Buttle, et al., *Bio. Chem. J.*, 32, 1101 (1938) and British Pat. No. 551,524. See also U.S. Pat. No. 4,118,742, Example 29(A). Acylation of the 2-aminobenzimidazole reactant with acetic, propionic, or butyric anhydride provides the respective 2-acetamido, 2-propionamido, or 2-butyramido benzimidazoles. The 2-formamidobenzimidazole reagents can be obtained by reacting the appropriate 2-aminobenzimidazole with the mixed anhydride obtained from formic acid and acetic anhydride. Alternatively, the 2-acylamino benzimidazole compounds can be prepared from the corresponding 2-aminobenzimidazole compounds by acylation with the appropriate acyl halide as described hereinabove.

The 2-unsubstituted benzimidazoles (I, $R_2$ is hydrogen) are prepared by heating the appropriate o-phenylenediamine with formic acid, usually in the presence of a mineral acid, such as hydrochloric acid. The 2-(1-hydroxyethyl) substituted benzimidazoles are similarly prepared using lactic acid instead of formic acid.

In the preparation of the preferred compounds where $R_6$ is phenyl or substituted phenyl, a preferred route of synthesis consists of the Friedel-Crafts acylation of 3,4-dinitrobenzoyl chloride upon the appropriately substituted benzene. The resulting 3,4-dinitrobenzophenone is then chemically or catalytically reduced to the corresponding 3,4-diaminobenzophenone which is then ring closed in the usual way.

The 2-methylmercaptobenzimidazole intermediates are prepared by treating the respective 2-thiobenzimidazole derivatives with methyl iodide in the presence of a weak base. The 2-thio compounds are prepared by heating the appropriate o-phenylenediamine with potassium ethyl xanthate in the usual manner.

The compounds of this invention wherein $R_2$ is hydroxy are prepared by condensing the appropriate o-phenylenediamine with a β-keto ester of formula

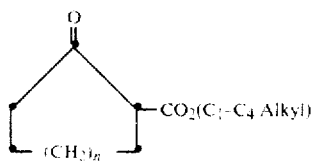

where n is 0–2, according to the method summarized in *Chemical Reviews*, 74 (3), 384 (1974), resulting both in ring closure to the 2-hydroxy benzimidazole and substitution on the nitrogen atom with a $C_5$–$C_7$ 1-cycloalkenyl substituent. Both 5- and 6-isomers are formed. The 2-hydroxy benzimidazole exists with its tautomer represented by the formula

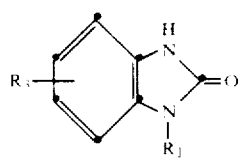

Additionally, N-substituted 5(6)-benzimidazoles may be prepared by the reaction of $R_1X$ with the appropriate o-phenylenediamine followed by ring closure in the usual manner.

All of the above procedures result in the preparation of isomeric mixtures of the 5- and 6-substituted benzimidazoles (I) of this invention. The mixture may be separated into the individual isomers, if desired, by chromatography and/or by fractional crystallization. Since the 6-isomer is usually preferred, a regiospecific synthesis is desirable to eliminate the extra purification steps and loss of half of the material as the undesired isomer. Such a procedure is outlined in Scheme I.

The o-nitrohalobenzene derivative III is reacted with $R_1NH_2$ at a temperature of 100°–200° C. to provide the corresponding aniline IV. For a volatile amine, the general procedure involves the reaction of the amine in a solvent, such as methanol, and heating in a stainless steel autoclave at about 140°–150° C. for about 16 hours. For non-volatile or aromatic amines, equal equivalents of III and $R_1NH_2$ are heated with anhydrous sodium carbonate in a high boiling nonreactive solvent, such as sulfolane. Heating for 3–4 hours at 100°–200° C. is usually adequate to give good yields of IV. When aromatic amines are used, a temperature range of 180°–200° C. is preferred.

The aniline IV is converted to diamine V by the usual methods of chemical or catalytic reduction. Preferably, the reduction is done through catalytic hydrogenation, in a non-reactive solvent such tetrahydrofuran, in the presence of a catalyst, such as Raney nickel.

The diamine V is then ring closed to the desired benzimidazole I in the manner previously described giving the single 5- or 6-isomer.

The required starting materials above, including $R_1X$, $R_1NH_2$, and III, are either commercially available or may be prepared by methods known in the literature. In the preferred case wherein $R_3$ is $Z=C(R_6)$- and $R_6$ is a phenyl derivative, the preferred method of preparing compounds of Formula III is the condensation of a phenyl acetonitrile with o-nitrochlorobenzene to give the intermediate 4-(phenylcyanomethylene)-2-chlorocyclohexa-2,5-diene-1-one oxime which upon oxidation with basic hydrogen peroxide gives III (X is chloro). The latter sequence was reported by Davis et al., *J. Org. Chem.*, 26, 4270 (1961) and Davis et al., *J. Am. Chem. Soc.*, 82, 2913 (1960).

Dialkylaminomethyl substituents can be introduced into the benzimidazoles by means of the Mannich reaction. The N-unsubstituted benzimidazole is allowed to react with the appropriate dialkylamine in the presence of formaldehyde to produce the desired N-(dialkylaminomethyl) derivatives of Formula I. If such derivatives are desired, the reaction is usually performed at the end of the synthesis because subsequent reaction steps, such as oxime formation, may remove the dialkylaminomethyl functionality.

Hydroxyimino derivatives can be prepared from the corresponding keto compounds (I, $R_3$ is $O=C(R_6)$—), by treatment with hydroxylamine in the usual manner. Similarly, the hydrazono derivatives can be prepared from the keto compounds by reacting with hydrazine.

The compounds of formula I, wherein $R_3$ is $Z=C(R_6)$— and Z is an acyloxyimine, are prepared by reacting the corresponding hydroxyiminobenzimidazole with the appropriate acylating agent (such as an anhydride).

The compounds of formula I wherein $R_3$ is $Z=C(R_6)$— and Z is an alkoxyamine are prepared by reacting the appropriate ketobenzimidazole with an alkoxyamine, or by alkylating the corresponding hydroxyiminobenzimidazole (suitable alkylating agents are an alkali metal alkoxide and alkyl halide).

When the oximes and oxime derivatives are prepared, the products are usually mixtures of the syn and anti isomers. The proportion of the anti isomer can be increased by conventional methods, e.g. fractional crystallization or high pressure chromatography. As the anti isomer is usually more active biologically, this enrichment process is useful.

The compounds of formula I wherein $R_3$ is $Z=C(R_6)-$ and Z is $C_1-C_7$ alkylidene, $=CHCN$, $=CHCONH_2$, and $=CHCO_2(C_1-C_4\ alkyl)$ are formed by the dehydration of the corresponding carbinol. Such dehydration reaction of a benzimidazole carbinol is depicted by the following generalized scheme:

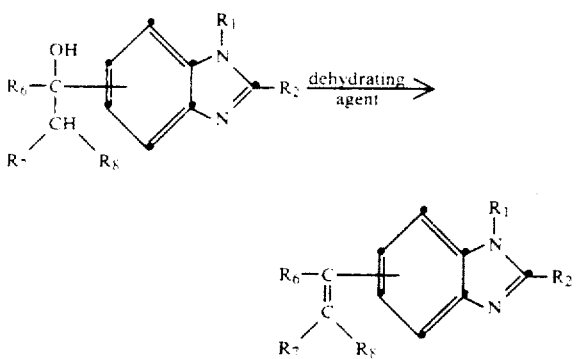

wherein $R_1$, $R_2$ and $R_6$ have the above-defined meanings, one of $R_7$ and $R_8$ is hydrogen and the other of $R_7$ and $R_8$ is hydrogen, $C_1-C_6$ alkyl, $-CN$, $-CONH_2$, or $-CO_2-(C_1-C_4\ alkyl)$ The dehydration of a benzimidazole carbinol according to the above scheme is accomplished by reaction of the carbinol with any of a number of dehydrating agents which are capable of removing a mole of water from each mole of carbinol to thus provide the corresponding olefinic benzimidazole of the invention. Typical dehydrating agents commonly used include acids such as sulfuric acid, hydrochloric acid, formic acid, polyphosphoric acid and p-toluenesulfonic acid. In a routine dehydration reaction, a carbinol is combined with about an equal weight amount or an excess of a dehydrating agent. The reaction normally is carried out in an organic solvent such as formic acid, chloroform, benzene, dichloromethane, or the like, at a temperature of about 20° C. to the reflux temperature of the particular solvent utilized for the reaction. Under these conditions, the dehydration typically is substantially complete within about one to about forty-eight hours. Longer reaction periods may be employed if desired. The reaction takes place in approximately two hours when the preferred conditions of refluxing formic acid are employed. Upon completion of the dehydration reaction, the product, an olefinic benzimidazole of the invention, can be isolated by simply washing the reaction mixture with a base, for instance dilute aqueous sodium bicarbonate or the like, and removing the organic reaction solvent by evaporation. The product can be further purified if desired by normal methods, including chromatography and crystallization from solvents such as ethanol, ethyl acetate, acetone, and the like.

It should be noted that when $R_7$ and $R_8$ in the above general formula defining the olefinic benzimidazoles of this invention are different, the compounds exist as cis (or Z) and trans (or E) isomers. The dehydration reaction described above generally provides a mixture of such isomers. For example, dehydration of a compound such as 1-isopropyl-2-amino-5-(α-hydroxy-α-cyanomethylbenzyl)benzimidazole affords a mixture of cis-1-isopropyl-2-amino-5-(α-cyanomethylenebenzyl)benzimidazole; and the corresponding trans isomer. The cis and trans isomers of the benzimidazoles provided herein are represented by the general formulas:

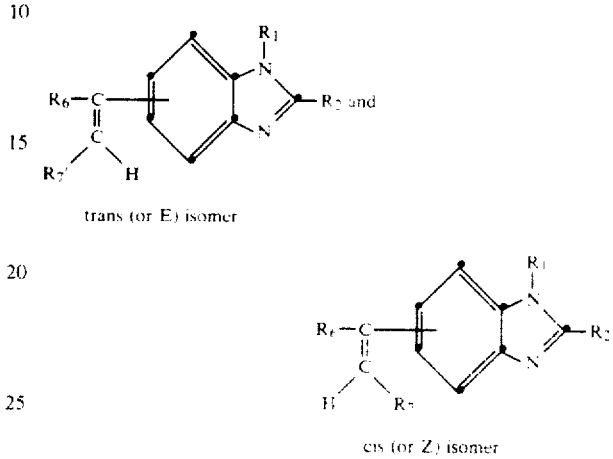

wherein $R_1$, $R_2$, and $R_6$ are as described hereinabove, and $R_7'$ is the same as $R_7$ (or $R_8$) but not hydrogen. Since both the cis and the trans olefinic benzimidazoles of this invention are potent antiviral agents, they can be utilized in the treatment of viral infections either alone or as a mixture.

Isolation of pure cis and pure trans olefinic benzimidazoles of the invention generally is accomplished by chromatography or by crystallization or fractional crystallization from solvents such as methanol, ethanol, acetone, or the like. The trans isomers usually appear more active than the cis compounds, and therefore are preferred over the cis isomers.

The benzimidazole carbinols which are the required starting materials in the above-described dehydration reaction are themselves antiviral agents and are provided in a further embodiment of this invention. Some of the carbinols are prepared by reaction of a 5- or 6-carbonyl substituted benzimidazole with a suitably substituted carbanion. For example, a carbanion of the formula $R_7''CH_2^\ominus$ reacts with a ketobenzimidazole of the formula

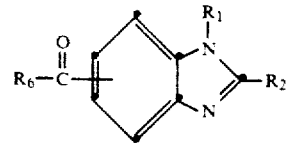

wherein $R_1$, $R_2$, and $R_6$ are the same as described herein above and $R_7''$ is $-CN$, $-CONH_2$, or $-CO_2(C_1-C_4\ alkyl)$ to form the corresponding benzimidazole carbinol. The ketobenzimidazoles are available by the methods described previously. The requisite carbanions are formed by reaction of an active methylene compound with a strong base such as methyl lithium, sodium hydride, n-butyl lithium, lithium diisopropylamide, potassium tert-butoxide, and the like. Active methylene compounds are those which have an electronegative functional group attached to a methyl or methylene group. Typical active methylene compounds which readily form carbanions include compounds of the formulas $CH_3CN$, $CH_3CONH_2$, and $CH_3CO_2(C_1-C_4\,alkyl)$. Protected forms of the active methylene compounds can also be employed; for instance, bis(trimethylsilyl)acetamide may be used in place of acetamide. Such compounds generally are reacted with about an equimolar quantity or an excess of strong base in an unreactive organic solvent such as diethyl ether, tetrahydrofuran, dimethylformamide, dioxane, diglyme, and the like. For example, an active methylene compound such as ethyl acetate can be reacted with a strong base such as n-butyl lithium in a solvent such as diethyl ether to form the corresponding carbanion, namely lithium ethoxycarbonylcarbanion. Such reactions typically are carried out at a temperature of about $-78°$ to about $-50°$ C., and are substantially complete within about one to about six hours.

Once the carbanion has formed, it typically is not isolated, but rather is reacted in situ with a ketobenzimidazole derivative. The carbanion generally is utilized in an excess of about 1 to about 10 molar compared to the ketobenzimidazole, and the reaction is routinely carried out at a temperature of about $-70°$ to about $30°$ C. The product of the reaction is the aforementioned carbinol benzimidazole, and can be isolated by simply acidifying the reaction mixture, for example with hydrochloric acid, and then removing the reaction solvent, for instance by evaporation under reduced pressure. Further purification of the carbinol benzimidazole generally is not needed, but if desired can be accomplished by routine procedures such as chromatography, crystallization, and the like.

The (αhydroxy-α-$C_1$-$C_7$ alkyl) derivatives are prepared by reacting the corresponding keto derivative with the appropriate Grignard reagent followed by hydrolysis in the usual manner.

The compounds of this invention wherein $R_3$ is $Z=C(R_6)$— and Z is =CHCl and =CHBr can be prepared by direct halogenation of a 5- or 6-(α-methylenemethyl)benzimidazole derivative. Such reaction can be depicted by the following general scheme:

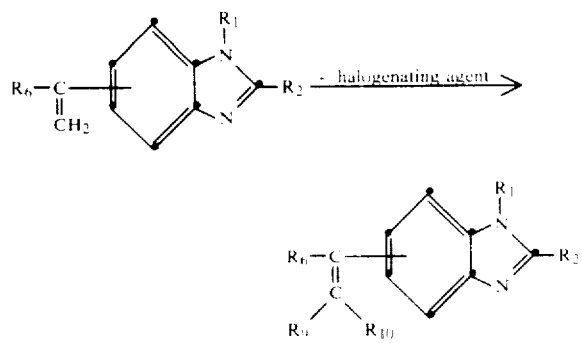

wherein $R_1$, $R_2$ and $R_6$ are as defined above, one of $R_9$ and $R_{10}$ is hydrogen and the other of $R_9$ and $R_{10}$ is chloro or bromo.

The methylenemethyl benzimidazoles which are required as starting materials for the halogenation reaction are prepared by the action of a methyl Grignard reagent on a ketobenzimidazole, followed by dehydration of the resulting carbinol, as discussed previously. The halogenating agents commonly utilized in the halo-genation reaction include N-chlorosuccinimide and N-bromosuccinimide. The halogenation reaction generally is carried out by combining the benzimidazole with the halogenating agent in a suitable unreactive organic solvent such as benzene, tetrahydrofuran, chloroform, toluene, diethyl ether, or related solvents. The use of about an equimolar quantity of halogenating agent effects monohalogenation to give a compound wherein one of $R_9$ and $R_{10}$ is bromo or chloro and the other is hydrogen. The use of a two molar amount or larger excess of halogenating agent effects dihalogenation and produces a compound wherein $R_9$ and $R_{10}$ both are halo. The reaction generally is carried out at a temperature of about 20° to about 80° C., and normally is complete within about one to about seventy-two hours at such temperature. The product is isolated by simply cooling the reaction mixture and removing the reaction solvent, for instance by evaporation under reduced pressure. The compounds thus prepared can be further purified if desired by chromatography, crystallization, or the like.

It will be appreciated that advantageous chemical reactions can be performed at optional stages of product synthesis. The benzimidazole reactant can be chemically modified and then reacted with the appropriate $R_1X$ to provide the desired product of Formula I. Alternatively, a $R_1$-substituted benzimidazole intermediate can be prepared and then chemically modified to provide the final product. Suitable benzimidazole reactants are those having substituent groups which can be converted to the desired 5(6)-substituents either prior to or after reaction with the appropriate $R_1X$.

The pharmaceutically acceptable acid addition salts of this invention include salts derived from inorganic acids such as hydrochloric acid, nitric acid, phosphoric acid, sulfuric acid, hydrobromic acid, hydroiodic acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate, and the like salts. Salts from inorganic acids are preferred, especially the hydrochloride salt.

The benzimidazole compounds of this invention were tested as pure compounds and as isomer mixtures. Both isomers inhibit virus growth, the 6-isomer generally being more active than the 5-isomer against the Polio I virus usually used for ascertaining biological activity.

As already pointed out, an additional embodiment of this invention is a pharmaceutical formulation useful in the treatment and prophylactic control of viral infections in mammals, especially humans. The formulations of this invention comprise a benzimidazole of the above general formula in combination with a pharmaceutical diluent, excipient or carrier therefor. The formulation of this invention will contain about 0.5 to about 95% by weight of active ingredient. The compounds may be formulated for convenient oral administration by being mixed with solid diluents such as lactose, sorbitol, mannitol, starch, including potato starch and corn starch, amylopectin, cellulose derivatives, magnesium stearate, calcium stearate, polyethyleneglycol waxes, polyvinylpyrrolidone, and related diluents and excipients. Such formulations ideally are compressed into tablets for convenient oral administration. Alternatively, the formulations may be encapsulated in gelatin capsules or the like, or may be molded into a tablet suited to sublingual administration. The 2-amino benzimidazole compounds of this invention are preferably administered by the oral route, while it is preferred that the 2-hydrogen compounds of this invention be administered by other than the oral route.

The compounds of the invention may also be administered rectally, and formulations suited to such administration ideally are prepared in the form of suppositories, which contain a benzimidazole of the invention admixed with a suitable neutral fat base or with a vegetable oil or paraffin oil.

Liquid preparations for oral administration may be prepared in the form of syrups or suspensions. Such formulations will contain about 0.5 to about 20 percent by weight of a compound of the invention, in combination with any of a number of suitable adjuvants such as sugar, ethanol, water, glycerol, propylene glycol and the like.

The benzimidazoles provided by this invention also may be administered parenterally to a mammal suffering from a viral infection or in need of prophylactic treatment. For such administration, solutions may be prepared by dissolving a compound of the invention, particularly as an acid addition salt, in a suitable solvent such as isotonic saline, aqueous glucose, or the like. The solutions will contain from about 0.5 to about 80 percent by weight of a benzimidazole of the invention, preferably about 1 to about 20 percent by weight.

The compounds of the invention may also be formulated as a nasal spray or inhaler. Such formulations will contain ideally about 0.5 to about 10 percent by weight of a benzimidazole. Nasal sprays will generally contain about 0.5 to about 5 percent by weight of active ingredient, and will contain carriers such as non-ionic polyoxyethylated oils, alcohols such as ethanol, flavor agents such as menthol, and propellants such as polyhalogenated methanes.

Yet another embodiment of this invention is a method of treating mammals, including humans, suffering from a viral infection or in need of prophylactic control of viral infections. The method includes treatment of domesticated animals such as swine, cattle, horses, and the like. The method comprises administering to a mammal an antiviral amount of a benzimidazole defined by the above general formula. As hereinabove pointed out, the compounds can be suitably formulated for convenient administration by any of several routes, including the oral and parenteral routes. While the particular dosage of active compound may vary depending upon the particular benzimidazole selected, the route of administration, the specific virus to be treated or guarded against, the tolerance of the host, and various other parameters known to the medical community, the general rule is that a benzimidazole of this invention will be administered in an antiviral amount, which generally is a dose of about 0.1 to about 500 mg./kg. of animal body weight. A typical dose of active compound will more preferably be about 0.5 to about 250 mg./kg., and ideally about 1 to about 100 mg./kg. Such dosage can be administered about once each day, or in the case of more severe viral infections, the dosage can be administered from two to three times each day or more often as required. Such repeated dosing may be especially desirable when a compound is formulated as a nasal spray.

Illustrative of the compounds provided by this invention are the following:
1-isopropyl-2-amino-5(6)-acetylbenzimidazole,
1-cyclopentyl-2-acetamido-5(6)-propionylbenzimidazole,
1-butyl-2-formamido-5(6)-(1-hydrazonooctyl)benzimidazole,
1-dimethylaminomethyl-2-methylmercapto-5(6)-[(α-butoxyimino)cycloheptylmethyl]benzimidazole,
1-morpholinylmethyl-5(6)-hydroxybenzimidazole,
1-piperidinylmethyl-2-formamido-5(6)-heptanoyloxybenzimidazole,
1-(N-methyl-N-propylaminomethyl)-2-butylamino-5(6)-(4-chlorobenzoyloxy)benzimidazole,
1-phenyl-2-propionamido-5(6)-[(1-methoxyimino-2-cyclopentyl)ethyl]benzimidazole,
1-(2-thiazolyl)-2-acetamido-5(6)-(3,4-dichlorobenzoyl)benzimidazole,
1-diisopropylaminomethyl-2-(1-hydroxyethyl)- 5(6)-[α-pentylidenebenzyl]benzimidazole,
1-cyclobutyl-2-propionamido-5(6)-hydroxybenzimidazole,
1-octyl-5(6)-phenylacetoxybenzimidazole,
1-piperidinylmethyl-2-methylmercapto-5(6)-(α-ethoxyiminocyclopentylmethyl)benzimidazole,
1-pentyl-2-acetamido-5(6)-heptanoylbenzimid-azole,
1-(1-cyclopentenyl)-2-hydroxy-5(6)-(α-hydrazonocyclopentylmethyl)benzimidazole,
1-cyclohexyl-2-amino-5(6)-(4-methoxybenzoyloxy)benzimidazole,
1-(4-methoxyphenyl)-5(6)-(α-hexylidenebenzyl)benzimidazole,
1-(1-adamantyl)-2-formamido-5(6)-(3-cyclopentylpropionyl)benzimidazole,
1-diethylaminomethyl-2-acetamido-5(6)-(1-ethoxyiminohexyl)benzimidazole,
1-ethyl-2-ethylamino-5(6)-[1-(4-fluorophenyl)- 0-cyanoethenyl]benzimidazole,
1-(N-ethyl-N-propylaminomethyl)-2-methylmercapto-5(6)-(α-n-butanoyloxyiminobenzyl)benzimidazole,
1-(morpholinylmethyl-2-(1-hydroxyethyl)-(6)-(1-phenyl-2-bromoethenyl)benzimidazole,
1-allyl-2-isopropylamino-5(6)-[1-(2,4,6-trimethylphenyl)heptylenyl]benzimidazole,
1-dipropylaminomethyl-2-acetamido-5(6)-(4-trifluoromethylbenzoyl)benzimidazole,
1-isopropyl-5(6)-(α-methoxyimino-3,4-dichlorobenzyl)benzimidazole,
1-(N-methyl-N-ethylaminomethyl)-2-amino-5(6)-(α-propoxyimino-2-iodo-4-butoxybenzyl)benzimidazole,
1-(1-cycloheptenyl)-2-hydroxy-5(6)-propionyloxybenzimidazole,
1-methyl-2-methylmercapto-5(6)-(α-hydrazono-3-butoxybenzyl)benzimidazole,
1-cyclopropyl-2-amino-5(6)-(4-butylbenzoyl)benzimidazole, 1-(2-pyridyl)-5(6)-(3-chloro-4-methoxybenzoyl)benzimidazole,
1-(2-thiazolyl)-2-ethylamino-5(6)-hydroxybenzimidazole,
1-t-butyl-2-(1-hydroxyethyl)-5(6)-(α-hydroxyimino-3-methoxybenzyl)benzimidazole,
1-benzyl-5(6)-(α-hydroxyimino-3-bromo-4-ethoxybenzyl)benzimidazole,
1-(3,5-dimethoxyphenyl)-2-amino-5(6)-pentanoyloxybenzimidazole, and
1-hexyl-2-formamido-5(6)-[(1-hydroxyimino-2-cyclobutyl)ethyl]benzimidazole.

In an effort to more fully illustrate the operation of this invention, the following detailed preparations and examples are provided. The examples are illustrative only and are not intended to limit the scope of the invention. The term "m/e" used in characterizing the products refers to the mass-to-charge ratio of ions which appear in the mass spectra of the products. In general, the values correspond to molecular weights of the major peaks, and are so designated "M+".

EXAMPLES 1 AND 2

1-Allyl-5-benzoylbenzimidazole and 1-allyl-6-benzoylbenzimidazole

To a solution of 8.8 g. of 5(6)-benzoylbenzimidazole in 150 ml. of dimethylformamide was added 5 ml. of allyl bromide. Two grams of a 50% sodium hydride suspension in oil were added and the reaction was stirred for about two hours at room temperature. The reaction mixture was poured into 300 ml. of ethyl acetate. The resulting suspension was washed three times with 300 ml. of a saturated sodium chloride solution and the organic layer was then evaporated to dryness, giving the title products as a mixture of the 5- and 6-isomers. Mass spectrum M+ =262.

Analysis: $C_{17}H_{14}N_2O$;
Calc.: C, 77.84; H, 5.38; N, 10.68;
Found: C, 77.92; H, 5.22; N, 10.46.

The individual isomers were separated by chromatography over silica gel eluting with 70–80% ethyl acetate/20–30% hexane. In the above example, 1.7 g. of the pure 5-isomer, 1.4 g. of the pure 6-isomer, and an additional amount of unresolved product were recovered by chromatography.

EXAMPLES 3–10

Following the procedure of Examples 1–2, the compounds of Table I were prepared using the appropriate benzimidazole and $R_1X$ halide.

Some of the products were converted to the hydrochloride salt in the usual way. Those compounds which are the hydrochloride salt are marked with an asterisk (*).

In the following tables, "W" refers to the substitution in the phenyl ring. Some of the compounds were not resolved into the pure isomers and are referred to as "5/6". Compounds which were resolved into the pure isomers are designated "5" or "6".

TABLE I

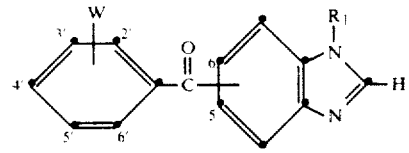

| Example No. | $R_1$ | Isomer | W | M+ | Calculated C | Calculated H | Calculated N | Found C | Found H | Found N |
|---|---|---|---|---|---|---|---|---|---|---|
| 3 | benzyl | 5/6 | H | 312 | 80.75 | 5.16 | 8.97 | 80.47 | 5.04 | 8.74 |
| 4 | phenyl | 6 | H | 298 | 80.52 | 4.73 | 9.39 | 78.99 | 4.17 | 8.45 |
| 5 | p-nitro-phenyl | 5/6 | H | 343 | 69.97 | 3.82 | 12.24 | 69.69 | 3.90 | 11.95 |
| 6 | isopropyl | 5/6 | H | 264 | 77.25 | 6.10 | 10.60 | 76.11 | 5.69 | 10.26 |
| 7* | isopropyl | 6 | H | 264 | 67.88 | 5.70 | 9.31 | 67.69 | 5.78 | 9.05 |
| 8* | isopropyl | 5 | 2',4',6'-trimethyl | 306 | 70.06 | 6.76 | 8.17 | 66.05 | 6.62 | 7.70 |
| 9* | isopropyl | 6 | 2',4',6'-trimethyl | 306 | 70.06 | 6.76 | 8.17 | 66.22 | 6.93 | 7.15 |
| 10 | morpholinylmethyl | 5/6 | H | 321 | 71.01 | 5.96 | 13.08 | 70.84 | 5.73 | 12.78 |

EXAMPLE 11

1-(2-pyridyl)-6-benzoylbenzimidazole

To a solution of 4.44 g. (20 mmoles) of (6)-benzoylbenzimidazole in 50 ml. of dimethylformamide was added 1.9 ml. (20 mmoles) of 2-chloropyridine. After adding 1 g. of sodium hydride (20 mmoles, 50% oil suspension), the reaction was heated to reflux overnight. The reaction was cooled and poured into ethyl acetate and the resulting suspension was washed three times with 300 ml. portions of a saturated sodium chloride solution. The organic solution was dried over magnesium sulfate and evaporated to dryness. The residue was chromatographed over silica gel eluting with 80% ethyl acetate/20% hexane, giving 1.01 g. of -(2-pyridyl)-5-benzoylbenzimidazole and 0.54 g. of -(2-pyridyl)-6-benzoylbenzimidazole. 1-(2-pyridyl)-5-benzoylbenzimidazole, M+ =299.

Analysis: $C_{13}H_{13}N_3O$;
Calc.: C, 76.24; H, 4.38; N, 14.04;
Found: C, 76.26; H, 4.66; N, 14.34.

1-(2-pyridyl)-6-benzoylbenzimidazole. M+ =299.
Analysis: $C_{13}H_{13}N_3O$;
Calc.: C, 76.24; H, 4.38; N, 14.04;
Found: C, 76.42; H, 4.28; N, 14.01.

EXAMPLE 12

1-(Dimethylaminomethyl)-5(6)-benzoylbenzimidazole

A 40% aqueous solution of dimethylamine (11.3 ml., 100 mmoles) was added to a suspension of 22.3 g. (100 mmoles) of 5(6)-benzoylbenzimidazole in 300 ml. of methylene chloride, followed by the dropwise addition of 15 ml. of a 37% aqueous solution of formaldehyde.

After stirring at room temperature for three days, the solution was extracted first with water, and then with 1 N sodium hydroxide. The organic phase was dried over magnesium sulfate and was then evaporated. The resulting residue was crystallized from ethyl acetate to give 17.2 g. of the title products. $M^+ = 279$.

Analysis: $C_{17}H_{17}N_3O$;
Calc.: C, 73.10; H, 6.13; N, 15.04;
Found: C, 72.53; H, 6.11; N, 14.05.

General Preparation 1

The following typical procedures were used to regioselectively prepare 5- and 6-substituted-2-aminobenzimidazole compounds of Formula I.

A. Reaction of a 3-chloro-4-nitrobenzophenone with $R_1NH_2$.

1. Procedure when $R_1NH_2$ is a volatile amine

Fifty grams of the 3-chloro-4-nitrobenzophenone, 100 ml. of the amine, and 300 ml. of methanol were heated to about 145° C. for 16 hours in a stainless steel autoclave. The reaction mixture was worked up by removing the solvent by evaporation, adding 6 N hydrochloric acid, and heating to reflux for about 20 minutes. Upon cooling, ethyl acetate was added and 5 N sodium hydroxide was added to a pH of about 9. The organic layer was separated, dried over magnesium sulfate, and evaporated. The product was purified by chromatography over silica gel eluting with 10% ethyl acetate/90% hexane. The 3-amino-4-nitrobenzophenone thus isolated was used without further purification for the subsequent step (B)

2. Procedure when $R_1NH_2$ is a non-volatile amine

About 15 g. of the chloronitrobenzophenone, 10 g. of anhydrous sodium carbonate, and one equivalent of the amine in 200 ml. of sulfolane were heated to 130°–140° C. for 3 to 3.5 hours and worked up as described above.

3. Procedure when $R_1NH_2$ is an aromatic amine

The conditions utilized were the same as for non-volatile amines, except that the reaction mixture was heated to 180°–190° C. for about 16 hours.

B. Hydrogenation of 3-amino-4-nitrobenzophenones to 3,4-diaminobenzophenones.

About 72 g. of the 3-amino-4-nitrobenzophenone were hydrogenated overnight in 2.9 L. of tetrahydrofuran under 60 psi at room temperature with about 15 g. of Raney nickel. The catalyst was removed by filtration and the solvent was removed in vacuo. The resulting diaminobenzophenone was used without purification for the subsequent steps.

C. Preparation of 2-aminobenzimidazoles.

Equal molar amounts of the 3,4-diaminobenzophenone and cyanogen bromide were stirred overnight in 90% methanol/10% water. The methanol was then removed in vacuo and ethyl acetate was added. The solution was washed once with a saturated solution of sodium bicarbonate. The solution was then dried and evaporated to a solid residue. Column chromatography over silica gel eluting with a 0–5% step gradient of methanol in ethyl acetate gave the desired product in about a 60% yield.

EXAMPLES 13–19

Following the procedures of General Preparation 1, the compounds of Table II were prepared.

TABLE II

| Example No. | $R_1$ | Isomer | W | $M^+$ | Calculated C | Calculated H | Calculated N | Found C | Found H | Found N |
|---|---|---|---|---|---|---|---|---|---|---|
| 13 | cyclohexyl | 6 | H | 319 | 75.21 | 6.63 | 13.16 | 73.22 | 6.81 | 13.60 |
| 14 | cyclohexyl | 6 | 4'-methoxy | 348# | 74.28 | 7.17 | 12.06 | 72.39 | 6.39 | 12.06 |
| 15 | cyclohexyl | 6 | 4'-fluoro | 336# | 70.35 | 5.90 | 12.95 | 71.41 | 5.69 | 12.49 |
| 16 | isopropyl | 6 | H | 279 | 73.10 | 6.13 | 15.04 | 70.32 | 6.31 | 13.30 |
| 17* | isopropyl | 6 | H | 279 | 64.66 | 5.75 | 13.31 | 61.71 | 5.74 | 12.30 |
| 18 | phenyl | 6 | H | 298# | 76.66 | 4.83 | 13.41 | 75.77 | 4.85 | 12.66 |
| 19 | allyl | 5 | H | 277 | Not determined | | | | | |

-m/e

General Preparation 2

Using the substituted diaminobenzophenones of General Preparation 1 (A and B), the 2-unsubstituted benzimidazoles of Examples 1–11 could be prepared by the reaction with formic acid giving the pure 5- and 6-isomers.

In a typical preparation, 50 g. of the diamine were mixed with 50 ml. of 98% formic acid and 100 ml. of 6 N hydrochloric acid. The mixture was refluxed for three hours, cooled, neutralized to a pH of about 7 with 2 N sodium hydroxide, and extracted with ethyl acetate. The organic layer was dried over magnesium sulfate and evaporated to dryness. The residue was purified by column chromatography over silica gel, eluting with 70% ethyl acetate/30% hexane. The usual yield of the pure isomers was about 50%.

EXAMPLE 20

1-isopropyl-2-(1-hydroxyethyl)-6-benzoylbenzimidazole

Reacting 3-isopropylamino-4-aminobenzophenone, prepared by General Preparation 1 (A and B), with lactic acid according to the procedure of General Preparation 2 gave the title product, $M^+ = 308$.
Analysis: $C_{19}H_{20}N_2O_2$;
Calc.: C, 74.00; H, 6.54; N, 9.08;
Found: C, 73.90; H, 6.40; N, 8.87.

EXAMPLES 21 AND 22

1-(1-cyclohexenyl)-2-hydroxy-5-benzoylbenzimidazole
and
1-(1-cyclohexenyl)-2-hydroxy-6-benzoylbenzimidazole Ten grams of 3,4-diaminobenzophenone and eight milliliters of ethyl 2-cyclohexanone carboxylate were refluxed overnight in xylene. The resulting precipitate was filtered hot to give 2.7 g. of 1-(1-cyclohexenyl)-2-hydroxy-5-benzoylbenzimidazole, $M^+ = 318$.

Analysis: $C_{20}H_{18}N_2O_2$;
Calc.: C, 75.45; H, 5.70; N, 8.80;
Found: C, 74.05; H, 5.17; N, 8.10.

The filtrate from above was cooled and concentrated in vacuo resulting in a precipitate which was recovered by filtration, affording 1.5 g. of pure 1-(1-cyclohexenyl)-2-hydroxy-6-benzoylbenzimidazole. $M^+ = 318$.

Analysis: $C_{20}H_{18}N_2O_2$;
Calc.: C, 75.45; H, 5.70; N, 8.80;
Found: C, 75.27; H, 5.68; N, 8.56.

EXAMPLE 23

2-methylmercapto-5(6)-benzoylbenzimidazole

A. Preparation of 2-thio-5(6)-benzoylbenzimidazole

Twenty grams (80.6 mmoles) of 3,4-diaminobenzophenone were dissolved in 300 ml. of methanol and 45 ml. of water. Potassium ethyl xanthate (12.9 g., 80.6 mmoles) was added and the reaction mixture was heated to reflux for three hours. Twelve grams of decolorizing charcoal were added and the reaction was refluxed an additional ten minutes. The reaction mixture was cooled and filtered and the solvent of the filtrate was removed by evaporation. Ethyl acetate (200 ml.) was added. The organic solution was washed twice with a saturated solution of sodium chloride and once with 1 N hydrochloric acid. The organic phase was dried over magnesium sulfate and evaporated to dryness. Crystallization of the residue from 30% ether/70% ethyl acetate gave 14.5 g. of 2-thio-5(6)-benzoylbenzimidazole.

B. Preparation of 2-methylmercapto-5(6)-benzoylbenzimidazole

Five grams of 2-thio-5(6)-benzoylbenzimidazole and five grams of sodium bicarbonate were added to 40 ml. of dimethylformamide, followed by 2.4 ml. of methyl iodide. After 15 minutes, the reaction mixture was added to 150 ml. of ethyl acetate.

The ethyl acetate solution was washed three times with a saturated solution of sodium chloride. The organic phase was dried over magnesium sulfate and evaporated. The resulting oil was washed with hexane to remove residual dimethylformamide, and the residue was crystallized from cold ether to give 1.7 g. of 2-methylmercapto-5(6)-benzoylbenzimidazole. $M^+ = 268$.

Analysis: $C_{15}H_{12}N_2OS$;
Calc.: C, 67.14; H, 4.51; N, 10.44; S, 11.95;
Found: C, 67.12; H, 4.89; N, 10.14; S, 11.97.

General Preparation 3

The following general preparation was used to convert ketones ($R_3$ is $O=C(R_6)-$) to the corresponding oximes.

One gram of the ketone is dissolved in 15 ml. of methanol and 5 ml. of pyridine. One gram of hydroxylamine hydrochloride is added and the reaction is refluxed for three hours. The reaction is added to a mixture of 200 ml. of ethyl acetate and 200 ml. of a saturated solution of sodium chloride. The pH is adjusted to about 7 with 1 N sodium hydroxide, and the organic layer is separated. The organic layer is dried over magnesium sulfate and evaporated. The desired oxime crystallizes on concentration of the solvent or the residue can be crystallized from small amounts of ethyl acetate. The reaction usually gives about a 50/50 mixture of the syn and anti isomers.

EXAMPLES 24–66

Following the procedure of General Preparation 3, the compounds of Examples 24–66 in Table III were prepared. Those examples marked with an asterisk (*) were converted to the hydrochloride salt from the free base in the following manner:

For oxime derivatives which were soluble in dilute hydrochloric acid, the oxime was dissolved in a minimum volume of 1 N hydrochloric acid and the solution brought to dryness in vacuo. The residue was crystallized from a small volume of acetone to give the desired product.

For oxime derivatives that are not soluble in 1 N hydrochloric acid, several equivalents of acetyl chloride was added to dry methanol, and the oxime was dissolved in the methanolic hydrogen chloride solution. Evaporation of the solvent gave the desired product which, if not already crystalline, could be crystallized from small volumes of acetone.

Some of the pure 5- and 6-isomers were prepared from the pure isomers of the corresponding ketone while others were resolved by crystallization and/or chromatography after a mixture of the oxime isomers was obtained by reacting hydroxylamine with a mixture of the 5- and 6-substituted ketones. All of the oxime derivatives were analyzed and tested as the mixture of syn and anti isomers.

TABLE III

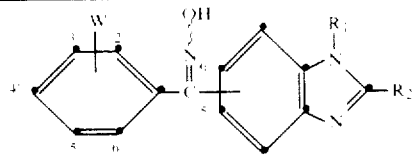

| Example No. | $R_1$ | $R_2$ | Isomer | W | M | Calculated C | H | N | Found C | H | N |
|---|---|---|---|---|---|---|---|---|---|---|---|
| 24 | isopropyl | H | 5,6 | H | 279 | 73.10 | 6.13 | 15.04 | 70.49 | 6.20 | 14.09 |
| 25* | isopropyl | H | 6 | H | 279 | 64.66 | 5.75 | 13.31 | 64.87 | 5.70 | 13.21 |
| 26 | isopropyl | H | 5 | H | 279 | 73.10 | 6.13 | 15.04 | 72.83 | 5.86 | 15.24 |
| 27* | isopropyl | H | 5 | H | 279 | 64.66 | 5.75 | 13.31 | 64.81 | 5.61 | 13.31 |

TABLE III-continued

| Example No. | R₁ | R₂ | Isomer | W | M⁺ | Calculated C | Calculated H | Calculated N | Found C | Found H | Found N |
|---|---|---|---|---|---|---|---|---|---|---|---|
| 28 | cyclohexyl | H | 5/6 | H | 319 | 75.21 | 6.63 | 13.16 | 74.98 | 6.56 | 13.44 |
| 29* | cyclohexyl | H | 6 | H | 319 | 67.50 | 6.23 | 11.81 | 68.27 | 6.41 | 9.30 |
| 30 | benzyl | H | 6 | H | 327 | 77.04 | 5.23 | 12.84 | 76.72 | 5.01 | 12.73 |
| 31 | benzyl | H | 5 | H | 327 | 77.04 | 5.23 | 12.84 | 74.58 | 5.19 | 12.60 |
| 32 | phenyl | H | 6 | H | 313 | 76.66 | 4.83 | 13.41 | 75.11 | 5.13 | 12.47 |
| 33* | phenyl | H | 6 | H | 313 | 68.67 | 4.61 | 12.01 | 67.40 | 4.93 | 11.12 |
| 34 | phenyl | H | 6 | 4'-chloro | 347 | 69.07 | 4.06 | 12.08 | 68.79 | 4.22 | 11.84 |
| 35 | p-nitrophenyl | H | 5/6 | H | 358 | 67.03 | 3.94 | 15.63 | 65.52 | 4.10 | 14.36 |
| 36** | p-aminophenyl | H | 5/6 | H | 328 | 73.15 | 4.91 | 17.06 | 70.43 | 5.33 | 15.68 |
| 37 | 2-pyridyl | H | 6 | H | 314 | 72.60 | 4.49 | 17.82 | 70.93 | 4.62 | 16.88 |
| 38 | 2-pyridyl | H | 5 | H | 314 | 72.60 | 4.49 | 17.82 | 72.00 | 4.76 | 16.98 |
| 39 | 1-adamantyl | H | 6 | H | 371 | 77.60 | 6.78 | 11.31 | 61.25 | 5.33 | 8.83 |
| 40 | cyclopropyl | H | 6 | H | 277 | 73.63 | 5.45 | 15.15 | 71.91 | 5.34 | 14.33 |
| 41 | n-hexyl | H | 6 | H | 321 | 74.74 | 7.21 | 13.07 | 74.72 | 7.28 | 12.92 |
| 42 | n-hexyl | H | 5 | H | 321 | 74.74 | 7.21 | 13.07 | 74.46 | 7.02 | 12.78 |
| 43 | allyl | H | 5 | H | 277 | 73.63 | 5.45 | 15.15 | 73.48 | 5.38 | 14.89 |
| 44 | allyl | H | 6 | H | 277 | 73.63 | 5.45 | 15.15 | 73.39 | 5.64 | 15.22 |
| 45 | 2-thiazolyl | H | 6 | H | 320 | 63.73 | 3.78 | 17.49 | 61.43 | 4.01 | 18.01 |
| 46 | morpholinylmethyl | H | 5/6 | H | 336 | 67.84 | 5.99 | 16.66 | 64.21 | 6.47 | 15.70 |
| 47 | CH₃CH(OH)CH₃ | H | 6 | H | 295 | 69.14 | 5.80 | 14.23 | 68.90 | 5.87 | 14.23 |
| 48 | t-butyl | H | 6 | H | 293 | 73.69 | 6.53 | 14.32 | 72.60 | 6.67 | 11.19 |
| 49 | cyclohexyl | NH₂ | 6 | H | 334 | 71.83 | 6.63 | 16.75 | 70.79 | 7.01 | 16.10 |
| 50 | cyclohexyl | NH₂ | 6 | 4'-methoxy | 363# | 69.40 | 6.38 | 15.42 | 65.35 | 6.29 | 14.01 |
| 51 | cyclohexyl | NH₂ | 6 | 3'-methyl | 348 | 72.39 | 6.94 | 16.08 | 72.39 | 7.14 | 15.76 |
| 52 | cyclohexyl | NH₂ | 6 | 2'-methyl | 348 | 72.39 | 6.94 | 16.08 | 71.61 | 7.02 | 15.18 |
| 53 | cyclohexyl | NH₂ | 6 | 4'-fluoro | 352 | 68.16 | 6.01 | 15.90 | 67.94 | 5.79 | 15.75 |
| 54 | 2-pyridyl | NH₂ | 6 | H | (D) | 69.29 | 4.59 | 21.26 | 63.91 | 4.25 | 20.41 |
| 55 | 1-adamantyl | NH₂ | 6 | H | 386 | 74.58 | 6.78 | 14.50 | 72.49 | 6.76 | 12.62 |
| 56* | isopropyl | NH₂ | 6 | H | 294 | 61.72 | 5.79 | 16.94 | 58.56 | 6.00 | 15.25 |
| 57 | CH₃CH(OH)CH₃ | NH₂ | 6 | H | 310 | 65.79 | 5.85 | 18.05 | 65.68 | 6.10 | 17.87 |
| 58 | isopropyl | NH₂ | 6 | H | 294 | 69.37 | 6.16 | 19.03 | 68.86 | 5.87 | 18.08 |
| 59 | phenyl | NH₂ | 6 | H | 313# | 76.66 | 4.83 | 13.41 | 75.11 | 5.13 | 12.47 |
| 60 | 2-pyridyl | NH₂ | 5 | H | 329 | 69.29 | 4.59 | 21.26 | 63.73 | 4.50 | 19.94 |
| 61 | allyl | NH₂ | 5 | H | 292 | | | | Not Determined | | |
| 62 | 1-cyclohexenyl | OH | 5 | H | 333 | 72.05 | 5.74 | 12.60 | 71.76 | 5.73 | 12.33 |
| 63 | 1-cyclohexenyl | OH | 6 | H | 333 | 72.05 | 5.74 | 12.60 | 72.25 | 5.77 | 12.32 |
| 64 | isopropyl | CH(OH)CH₃ | 6 | H | *** | 70.57 | 6.55 | 12.99 | 67.69 | 7.35 | 10.88 |
| 65 | benzyl | SCH₃ | 5 | H | 373 | 70.75 | 5.13 | 11.25 | 70.55 | 4.93 | 11.33 |
| 66 | benzyl | SCH₃ | 6 | H | 373 | 70.75 | 5.13 | 11.25 | 70.56 | 4.92 | 11.15 |

*hydrochloride salt
**prepared from the p-nitrophenyl derivative, Ex. 35, by reduction.
***Not determined
D m/e = 252 (M⁺ – ??)
m/e

EXAMPLE 67

1-(dimethylaminomethyl)-5(6)-(α-hydroxyiminobenzyl)benzimidazole

To a suspension of 7.11 g. (30 mmoles) of 5(6)-(α-hydroxyiminobenzyl)benzimidazole, in 90 ml. of methylene chloride was added 3.4 ml. of a 40% aqueous solution of dimethylamine, followed by 4.5 ml. of a 37% aqueous solution of formaldehyde. The reaction was stirred for three days at room temperature and then washed with 100 ml. of 1 N sodium hydroxide. The organic layer was separated, dried over magnesium sulfate, and removed by evaporation to give a gum. Crystallization of the gum from 20 ml. of 50% aqueous methanol gave 1.95 g. of a mixture of the title isomers.

Analysis: $C_{17}H_{18}N_4O$;
Calc.: C, 67.37; H, 6.16; N, 19.03;
Found: C, 68.27; H, 6.21; N, 18.32.

EXAMPLE 68

1-isopropyl-2-isopropylamino-5(6)-(α-hydroxyiminobenzyl)benzimidazole

When 2-amino-5(6)-benzoylbenzimidazole was treated with two equivalents of sodium hydride and an excess of isopropyl bromide according to the procedure of Examples 1–2, the dialkylated 1-isopropyl-2-isopropylamino-5(6)-benzoylbenzimidazole products were obtained. Treatment of this intermediate with hydroxylamine hydrochloride according to the procedure of Preparation 3 gave the title products as an isomeric mixture, M+ = 336.

Analysis: C₂₀H₂₄N₄O; Calc.: C, 71.40; H, 7.19; N, 16.65; Found: C, 71.63; H, 7.24; N, 16.47.

EXAMPLE 69

1-isopropyl-2-amino-6-(1-phenylethenyl)benzimidazole

Three grams (10.7 mmoles) of 1-isopropyl-2-amino-6-benzoylbenzimidazole were dissolved in 25 ml. of tetrahydrofuran, after which was added 27 ml. of a 2M solution of methyl magnesium bromide in ethyl ether. After stirring overnight, ethyl acetate was added, and the solution was washed three times with a saturated sodium chloride solution. The organic solution was dried over magnesium sulfate, filtered, and evaporated under reduced pressure. One hundred milliliters of 98% formic acid were added to the residue. The solution was refluxed for 2 hours. The formic acid was evaporated under reduced pressure. Ethyl acetate was added, and the resulting solution was washed with a saturated sodium bicarbonate solution. After drying over magnesium sulfate, the solution was filtered and concentrated. Upon the addition of a small volume of ether, 2.0 g. of the title product solidified out of solution which was recovered by filtration, M+ = 277.

Analysis: C₁₈H₁₉N₃; Calc.: C, 77.95; H, 6.90; N, 15.15; Found: C, 76.90; H, 6.99; N, 14.03.

EXAMPLE 70

1-isopropyl-2-amino-6-(1-phenyl-1-propenyl)benzimidazole

Following the procedure of Example 69, 1-isopropyl-2-amino-6-benzoylbenzimidazole and ethyl magnesium bromide were reacted to give the title product as both the cis and trans alkylene isomers, M+ = 291.

Analysis: C₁₉H₂₁N₃; Calc.: C, 78.32; H, 7.26; N, 14.42; Found: C, 73.67; H, 7.10; N, 12.27.

EXAMPLE 71

1-isopropyl-2-amino-6-(1-phenyl-2-bromoethenyl)benzimidazole

Three hundred milligrams (1.08 mmoles) of 1-isopropyl-2-amino-6-(1-phenylethenyl)benzimidazole and 192 mg. (1.08 mmoles) of N-bromosuccinimide were refluxed overnight in 20 ml. of dry tetrahydrofuran. After cooling, ethyl acetate was added and the solution was washed with a saturated solution of sodium bicarbonate. The organic layer was dried over magnesium sulfate, filtered, and evaporated in vacuo. The residue was chromatographed over silica gel, first eluting with ethyl acetate to remove impurities, and then with 10% methanol/90% ethyl acetate. The title product was crystallized from ether giving 200 mg. of the cis/trans mixture, M+ = 357.

Analysis: C₁₈H₁₈BrN₃; Calc.: C, 60.68; H, 5.09; N, 11.79; Br, 22.43; Found: C, 60.58; H, 5.24; N, 11.95; Br, 22.13.

EXAMPLE 72

1-isopropyl-2-amino-6-(1-phenyl-2-cyanoethenyl)benzimidazole

Forty millimoles (2.1 ml.) of dry acetonitrile were added to 30 ml. of tetrahydrofuran. A nitrogen blanket was applied and the temperature of the solution lowered to about −78° C. by means of an external acetone/dry ice bath. Twenty-five milliliters of a 1.6M solution of n-butyl lithium were added. After stirring at −78° C. for 30 minutes, a solution of 2.8 g. (10 mmoles) of 1-isopropyl-2-amino-6-benzoylbenzimidazole in 30 ml. of tetrahydrofuran was added. The reaction solution was allowed to warm to about −20° C. and was then stirred for 5 hours at −20° to −5° C. Water and ethyl acetate were then added and the layers were separated. The organic layer was dried over magnesium sulfate, filtered, and evaporated in vacuo. The residue was dissolved in 100 ml. of 98% formic acid. After stirring on a hot water bath for 2.5 hours, the solution was evaporated under reduced pressure. The residue was dissolved in ethyl acetate and washed with a saturated solution of sodium bicarbonate. The organic solution was dried over magnesium sulfate, filtered, and evaporated. The residue was chromatographed over silica gel, eluting first with ethyl acetate to remove non-polar impurities, then with 10% methanol/90% ethyl acetate to elute the title product. The product was further purified by reverse phase chromatography, eluting with 60% aqueous methanol, followed by crystallization from methyl ethyl ketone, resulting in 350 mg. of the title product, M+ = 302.

Analysis: C₁₉H₁₈N₄; Calc.: C, 75.47; H, 6.00; N, 18.53; Found: C, 70.45; H, 5.99; N, 15.50.

EXAMPLE 73

1-phenyl-2-amino-6-(1-phenyl-2-cyanoethenyl)benzimidazole

Following the procedure of Example 72, 3.1 g. of 1-phenyl-2-amino-6-benzoylbenzimidazole was transformed into 300 mg. of the title product, M+ = 336.

Analysis: C₂₂H₁₆N₄; Calc.: C, 78.55; H, 4.79; N, 16.66; Found: C, 78.51; H, 4.52; N, 16.85.

EXAMPLE 74 anti-3-(1-isopropyl-2-aminobenzimidazol-6-yl)-3-phenyl-2-propenamide hydrochloride A solution of 8.37 g. of 1-isopropyl-2-amino-6-benzoylbenzimidazole in tetrahydrofuran was added to a solution of 95 ml. of a 1.6M solution of n-butyl lithium and 30.45 g. of bis(trimethylsilyl)acetamide in tetrahydrofuran which was previously cooled to about −70° C. The reaction was stirred for about two hours and the temperature was allowed to warm to about −10° C. The reaction was poured into an ice/ammonium chloride solution. The organic layer was separated, washed with water, and dried, giving both the syn- and anti-isomers of the title compound. The residue was dissolved in a small volume of methyl ethyl ketone. After standing at room temperature overnight, the resulting crystals were recovered by filtration and identified as syn-3-(1-isopropyl-2-aminobenzimidazol-6-yl)-3-phenyl-2-propenamide, M+ = 320.

Analysis: C₁₉H₂₀N₄O; Calc.: C, 71.24; H, 6.47; N, 17.27; O, 5.19; Found: C, 71.23; N, 6.29; N, 17.49; O, 4.99.

The mother liquor from the above product was evaporated, and the residue was dissolved in pyridine. Excess thionyl chloride was added and the solution was stirred at room temperature overnight. The reaction mixture was evaporated to dryness in vacuo. Water and ethyl acetate were added to the residue. The layers were separated and the water layer was adjusted to a pH of about 8. The water layer was extracted with ethyl acetate. The ethyl acetate was dried and evaporated to dryness to give the title anti-3-(1-isopropyl-2-aminobenzimidazol-6-yl)-3-phenyl-2-propenamide hydro-chloride.

Analysis: C₁₉H₂₀N₄O·HCl; Calc.: C, 63.19; H, 6.03; N, 15.04; O, 6.30; Cl, 9.74; Found C, 63.95; H, 5.93; N, 15.70; O, 4.48; Cl, 9.93.

The following formulation examples may employ as active ingredients any of the pharmaceutical compounds of this invention.

EXAMPLE 75

| Preparation of Tablets | |
|---|---|
| | Per Tablet |
| 1-cyclohexyl-2-amino-6-(α-hydroxyiminobenzyl)benzimidazole | 250 mg |
| Lactose | 200 mg |
| Corn starch | 300 mg |
| Corn starch paste | 50 mg |
| Calcium stearate | 5 mg |
| Dicalcium phosphate | 45 mg |

The benzimidazole, corn starch, lactose and dicalcium phosphate are uniformly blended. The corn starch paste is prepared as a 10 percent aqueous paste and is blended into the mixture to uniformity. The mixture is blended with the calcium stearate and then compressed in tablets each weighing 850 mg.

EXAMPLE 76

| Preparation for Suppositories | |
|---|---|
| | Per suppository |
| 1-isopropyl-5-acetylbenzimidazole | 500 mg |
| Theobroma oil | 1500 mg |

The above ingredients are blended to uniformity at a temperature of about 60° C., poured into a suppository mold of nominal 2 g. capacity, and allowed to cool.

EXAMPLE 77

| Preparation for Oral Suspension | |
|---|---|
| | Per 100 ml. |
| 1-Ethyl-2-acetamido-6-(1-phenyl-2-bromoethenyl)benzimidazole | 500 mg |
| Sorbitol solution (70% N.F.) | 40 ml |
| Sodium benzoate | 150 mg |
| Lactose | 10 mg |
| Cherry flavor | 50 mg |
| Water | q.s. to 100 ml |

The above ingredients are combined such that each ml. of syrup contains 5 mg. of active ingredient.

EXAMPLE 78

| Intranasal Formulation | |
|---|---|
| | Percent by weight |
| 1-(4-methoxyphenyl)-2-methyl-mercapto-6-[(α-ethenyl)-cyclohexylmethyl]benzimidazole | 1.0 |
| Antarox (non-ionic polyoxyethylated fixed oil, GAF Corp.) | 38.5 |
| Ethanol | 10.0 |
| Freon 11 (trichloromonofluoromethane) | 25.0 |
| Freon 12 (dichlorodifluoromethane) | 25.0 |

| -continued | |
|---|---|
| Intranasal Formulation | |
| | Percent by weight |
| Menthol | 0.5 |

The benzimidazole is added to the Antarox at about 70°-80° C. and the mixture is stirred until a solution is formed. The solution is cooled and diluted with a mixture of the methanol in the ethanol. The resulting solution is placed in an aerosol container and chilled to 0° C., the Freon propellants are added, and the aerosol container is sealed with a valve.

The compounds of this invention were tested by the following method.

African green monkey kidney cells (BSC-1) or Hela cells (S-3) were grown in 25 cc. Falcon flasks at 37° C. in medium 199 with 5 percent inactivated fetal bovine serum (FBS), penicillin (150 units per ml.) and streptomycin (150 mcg./ml.). When confluent monolayers were formed, the supernatant growth medium was removed and 0.3 ml. of an appropriate dilution of virus (echo, Mengo, Coxsackie, polio or rhinovirus) was added to each flask. After absorption for one hour at room temperature, the virus infected cell sheet was overlaid with a medium comprising one part of 1 percent Ionagar No. 2 and one part double strength medium 199 with FBS, penicillin, and streptomycin which contains test compound at concentrations of about 100, 50, 25, 12, 6, 3, 1.5, 0.75, and 0, and/or 12.5, 6.25, 3.12, 1.56, 0.78, 0.39, 0.19, 0.09, 0.04, and 0.02 micrograms per milliliter (mcg./ml.). The flask containing no test compound served as the control for the test. The stock solutions of benzimidazole compounds were made up in dimethylsulfoxide solution at a concentration of $10^4$ mcg./ml. The flasks were incubated for 72 hours at 37° C. for polio, Coxsackie, echo, and Mengo virus and 120 hours at 32° C. for rhinovirus. Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each test concentration. The activity of the test compound was expressed as percentage plaque reduction, or percent inhibition. Alternatively, the test concentration which inhibits plaque formation by 50 percent can be used as a measure of activity. The 50 percent inhibition is indicated by the symbol $I_{50}$.

Test results are expressed in terms of Polio virus type I inhibition because the virus is easy to grow and consistent test results are obtained. However, the activity of the preferred compounds was confirmed against other virus cultures such as Coxsackie (A9, A21, B5), echovirus (strains 1-4), Mengo, rhinovirus (25 strains) and Polio (type I, II, III). Test results for various benzimidazole compounds are summarized in Table IV below where column 1 gives the Example number from the previous chemical examples, column 2 gives the 5(6)-position of the corresponding benzimidazole product, and column 3 indicates the test compound concentration in micrograms per milliliter (mcg./ml.) which inhibits Polio I plaque formation by 50 percent ($I_{50}$). In each case, 1-isopropylsulfonyl-2-amino-6-(syn-α-hydroxyiminobenzyl)benzimidazole was tested as a standard reference and gave an $I_{50}$ in the range of 0.2–0.8 mcg./ml.

TABLE IV

Polio I Plaque Reduction of 1-Substituted-5(6)-Substituted-Benzimidazoles

| Example No. | Isomer | $I_{50}$ (mcg./ml.)** |
|---|---|---|
| 2 | 6 | 0.78 |
| 6 | 5/6 | 6.0 |
| 8 | 5 | 6.25 |
| 9 | 6 | 6.25 |
| 10 | 5/6 | 25 |
| 11 | 6 | 12.5 |
| 12 | 5/6 | 12.5 |
| 18 | 6 | 0.78 |
| 21 | 5 | >100 |
| 22 | 6 | 6 |
| 24 | 5/6 | 0.19 |
| 25* | 6 | 0.39 |
| 26 | 5 | 25 |
| 27* | 5 | 25 |
| 28 | 5/6 | 0.19 |
| 29* | 6 | 0.78 |
| 30 | 6 | 0.39 |
| 31 | 5 | 25 |
| 32 | 6 | 0.09 |
| 33* | 6 | 0.09 |
| 34 | 6 | 0.19 |
| 35 | 5/6 | 0.75 |
| 36 | 5/6 | 0.09 |
| 37 | 6 | 0.75 |
| 38 | 5 | >100 |
| 39 | 6 | 25 |
| 40 | 6 | 0.39 |
| 41 | 6 | 0.78 |
| 42 | 5 | 100 |
| 44 | 6 | 0.78 |
| 45 | 6 | 0.78 |
| 46 | 5/6 | 6 |
| 47 | 6 | 6.25 |
| 48 | 6 | 0.19 |
| 49 | 6 | 0.09 |
| 50 | 6 | 0.09 |
| 51 | 6 | 3.12 |
| 52 | 6 | 0.78 |
| 53 | 6 | 1.5 |
| 54 | 6 | 6 |
| 55 | 6 | 0.75 |
| 57 | 6 | 3.12 |
| 58 | 6 | 0.09 |
| 59 | 6 | 0.09 |
| 60 | 5 | 6 |
| 62 | 5 | 3 |
| 63 | 6 | 3 |
| 64 | 6 | 1.5 |
| 65 | 5 | 50 |
| 66 | 6 | 25 |
| 67 | 5/6 | 6 |
| 68 | 5/6 | 3 |
| 69 | 6 | 1.56 |
| 70 | 6 | 0.78 |
| 71 | 6 | 0.09 |
| 72 | 6 | 0.04 |
| 74* | 6 | 0.39 |

*hydrochloride salt
**Drug concentration in micrograms per milliliter

I claim:
1. A compound of the formula

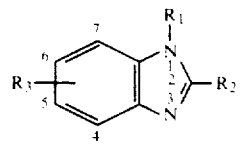

or a pharmaceutically acceptable salt thereof, wherein
$R_1$ is $C_1$–$C_8$ alkyl, $C_2$–$C_8$ alkenyl, $C_3$–$C_7$ cycloalkyl, $C_5$–$C_7$ 1-cycloalkenyl, adamantyl, hydroxy-substituted $C_1$–$C_8$ alkyl, unsubstituted or substituted phenyl, or unsubstituted or substituted benzyl;

$R_2$ is hydrogen, amino, $C_1$–$C_4$ alkylamino, methylmercapto, hydroxy, $C_1$–$C_4$ carboxylic acylamino, or 1-hydroxyethyl;

$R_3$ is

Z is oxygen, hydroxyimino, $C_1$–$C_4$ alkoxyimino, $C_1$–$C_4$ carboxylic acyloxyimino, hydrazono, $C_1$-$C_7$ alkylidene, =CHBr, =CHCl, =CHCN, =CHCONH$_2$, or =CHCO$_2$($C_1$-$C_4$ alkyl);

R$_6$ is $C_1$-$C_7$ alkyl, $C_3$-$C_7$ cycloalkyl, ($C_3$-$C_7$ cycloalkyl)methyl, 2-($C_3$-$C_7$ cycloalkyl)ethyl, unsubstituted or substituted benzyl, or unsubstituted or substituted phenyl wherein the substituents on the phenyl and benzyl rings are one to three of $C_1$-$C_4$ alkyl, $C_1$-$C_4$ alkoxy, fluoro, chloro, bromo, iodo, nitro, amino or trifluoromethyl; and R$_3$ is at the 5 or 6 position, subject to the limitation that when R$_2$ is hydroxy, R$_1$ may only be $C_5$-$C_7$ 1-cycloalkenyl.

2. A compound of claim 1 wherein R$_1$ is $C_1$-$C_8$ alkyl.
3. A compound of claim 2 wherein R$_1$ is isopropyl.
4. A compound of claim 1 wherein R$_1$ is $C_2$-$C_8$ alkenyl.
5. A compound of claim 1 wherein R$_1$ is phenyl.
6. A compound of claim 1 wherein R$_2$ is hydrogen.
7. A compound of claim 1 wherein R$_2$ is amino.
8. A compound of claim 1 wherein R$_1$ is $C_3$-$C_7$ cycloalkyl.
9. A compound of claim 8 wherein R$_1$ is cyclohexyl.
10. A compound of claim 1 wherein R$_3$ is phenyl.
11. A compound of claim 1 wherein R$_6$ is substituted phenyl.
12. A compound of claim 1 wherein Z is oxygen.
13. A compound of claim 1 wherein Z is hydroxyimino.
14. A compound of claim 1 wherein Z is =CHBr.
15. A compound of claim 1 wherein Z is =CHCN.
16. A compound of claim 1 wherein Z is =CHCH$_3$.
17. A compound of claim 1 wherein Z is =CHCONH$_2$.
18. A compound of claim 1 wherein R$_3$ is at the 6 position.
19. The compound of claim 16 which is 1-isopropyl-2-amino-6-(1-phenyl-1-propenyl)benzimidazole or a pharmaceutically acceptable salt thereof.
20. The compound of claim 15 which is 1-isopropyl-2-amino-6-(1-phenyl-2-cyanoethenyl)benzimidazole or a pharmaceutically acceptable salt thereof.
21. The compound of claim 15 which is 1-phenyl-2-amino-6-(1-phenyl-2-cyanoethenyl)benzimidazole or a pharmaceutically acceptable salt thereof.
22. The compound of claim 14 which is 1-isopropyl-2-amino-6-(1-phenyl-2-bromoethenyl)benzimidazole or a pharmaceutically acceptable salt thereof.
23. The compound of claim 17 which is 3-(1-isopropyl-2-amino-benzimidazol-6-yl)-3-phenyl-2-propenamide or a pharmaceutically acceptable salt thereof.
24. The compound of claim 13 which is 1-isopropyl-2-amino-6-(α-hydroxyiminobenzyl)benzimidazole or a pharmaceutically acceptable salt thereof.
25. The compound of claim 5 which is 1-phenyl-amino-6-(α-hydroxyiminobenzyl)benzimidazole or a pharmaceutically acceptable salt thereof.
26. The compound of claim 9 which is 1-cyclohexyl-2-amino-6-(α-hydroxyiminobenzyl)benzimidazole or a pharmaceutically acceptable salt thereof.
27. The compound of claim 6 which is 1-(tertbutyl)-6-(α-hydroxyiminobenzyl)benzimidazole or a pharmaceutically acceptable salt thereof.
28. A pharmaceutical formulation useful in the treatment and prophylactic control of viral infections in mammals comprising a pharmaceutically acceptable diluent or carrier in combination with an effective antiviral amount of a benzimidazole of claim 1.

29. A formulation according to claim 28 comprising a compound wherein R$_1$ is $C_1$-$C_8$ alkyl.
30. A formulation according to claim 29 comprising a compound wherein R$_1$ is isopropyl.
31. A formulation according to claim 28 comprising a compound wherein R$_1$ is $C_2$-$C_8$ alkenyl.
32. A formulation according to claim 28 comprising a compound wherein R$_1$ is phenyl.
33. A formulation according to claim 28 comprising a compound wherein R$_2$ is hydrogen.
34. A formulation according to claim 28 comprising a compound wherein R$_2$ is amino.
35. A formulation according to claim 28 comprising a compound wherein R$_1$ is $C_3$-$C_7$ cycloalkyl.
36. A formulation according to claim 48 comprising a compound wherein R$_1$ is cyclohexyl.
37. A formulation according to claim 28 comprising a compound wherein R$_6$ is phenyl.
38. A formulation according to claim 28 comprising a compound wherein R$_6$ is substituted phenyl.
39. A formulation according to claim 28 comprising a compound wherein Z is oxygen.
40. A formulation according to claim 28 comprising a compound wherein Z is hydroxyimino.
41. A formulation according to claim 28 comprising a compound wherein R$_3$ is at the 6 position.
42. A method of treating or preventing viral infections in mammals comprising administering to a mammal suffering from or exposed to a viral infection and in need of treatment an effective antiviral amount of a compound of the formula or a pharmaceutically acceptable salt thereof, wherein
R$_1$ is $C_1$-$C_8$ alkyl, $C_2$-$C_8$ alkenyl, $C_3$-$C_7$ cycloalkyl, $C_5$-$C_7$ 1-cycloalkenyl, adamantyl, hydroxy-substituted $C_1$-$C_8$ alkyl, unsubstituted or substituted phenyl, or unsubstituted or substituted benzyl;

R$_2$ is hydrogen, amino, $C_1$-$C_4$ alkylamino, methylmercapto, hydroxy, $C_1$-$C_4$ carboxylic acylamino, or 1-hydroxyethyl;

R$_3$ is $C_2$-$C_8$ alkanoyloxy, unsubstituted or substituted phenylacetoxy, unsubstituted or substituted benzoyloxy, or $$R_6C\overset{\|}{\underset{Z}{-}};$$

Z is oxygen, hydroxyimino, $C_1$-$C_4$ alkoxyimino, $C_1$-$C_4$ carboxylic acyloxyimino, hydrazono, $C_1$-$C_7$ alkylidene, =CHBr, =CHCl, =CHCN, =CHCONH$_2$, or =CHCO$_2$($C_1$-$C_4$ alkyl);

R$_6$ is $C_1$-$C_7$ alkyl, $C_3$-$C_7$ cycloalkyl, ($C_3$-$C_7$ cycloalkyl)methyl, 2-($C_3$-$C_7$ cycloalkyl)ethyl, unsubstituted or substituted benzyl, or unsubstituted or substituted phenyl wherein the substituents on the phenyl, benzyl, phenylacetoxy and benzoyloxy rings are one to three of $C_1$-$C_4$ alkyl, $C_1$-$C_4$ alkoxy, fluoro, chloro, bromo, iodo, nitro, amino or trifluoromethyl; and R$_3$ is at the 5 or 6 position, subject to the limitation that when $R_2$ is hydroxy, $R_1$ may only be $C_5$-$C_7$ 1-cyclolkenyl.

43. A method according to claim 42 employing a compound wherein $R_1$ is $C_1$-$C_8$ alkyl.

44. A method according to claim 42 employing a compound wherein $R_1$ is $C_2$-$C_8$ alkenyl.

45. A method according to claim 42 employing a compound wherein $R_1$ is phenyl.

46. A method according to claim 42 employing a compound wherein $R_2$ is hydrogen.

47. A method according to claim 42 employing a compound wherein $R_2$ is amino.

48. A method according to claim 42 employing a compound wherein $R_1$ is $C_3$-$C_7$ cycloalkyl.

49. A method according to claim 42 employing a compound wherein $R_3$ is $Z=C(R_6)-$.

50. A method according to claim 49 employing a compound wherein $R_6$ is phenyl.

51. A method according to claim 49 employing a compound wherein Z is oxygen.

52. A method according to claim 49 employing a compound wherein Z is hydroxyimino.

53. A method according to claim 42 employing a compound wherein $R_3$ is at the 6 position.

* * * * *

UNITED STATES PATENT AND TRADEMARK OFFICE
CERTIFICATE OF CORRECTION

PATENT NO. : 4,492,708
DATED : January 8, 1985
INVENTOR(S) : Wayne A. Spitzer

It is certified that error appears in the above—identified patent and that said Letters Patent is hereby corrected as shown below:

Claim 10, column 29, line 23, "$R_3$" should -- $R_6$ --.

Claim 36, column 30, line 16, "claim 48" should read -- claim 35 --.

Signed and Sealed this

Twelfth Day of January, 1988

Attest:

DONALD J. QUIGG

*Attesting Officer*   *Commissioner of Patents and Trademarks*